United States Patent [19]

Wu et al.

[11] 4,151,194
[45] Apr. 24, 1979

[54] DICYANOTRICYCLODECANE

[75] Inventors: Ching-Yong Wu, O'Hara Township, Allegheny County; Harold E. Swift, Gibsonia, both of Pa.

[73] Assignee: Gulf Research & Development Company, Pittsburgh, Pa.

[21] Appl. No.: 859,386

[22] Filed: Dec. 12, 1977

[51] Int. Cl.$^2$ .................. C07C 120/02; C07C 121/46
[52] U.S. Cl. ............................ 260/464; 260/453 AP; 260/465.3; 260/563 P; 528/74; 528/272; 528/310; 528/344; 568/817
[58] Field of Search ............................ 260/464, 465.3

[56] References Cited

U.S. PATENT DOCUMENTS

| | | | |
|---|---|---|---|
| 3,778,462 | 12/1973 | Taylor et al. | 260/465.3 |
| 3,925,445 | 12/1975 | King et al. | 260/465.3 X |
| 3,928,414 | 12/1975 | Shimizu et al. | 260/464 X |
| 3,960,920 | 6/1976 | Ohotsubo | 260/464 |
| 3,992,433 | 11/1976 | Ariyoshi et al. | 260/464 X |
| 4,076,748 | 2/1978 | Hoffmann et al. | 260/464 X |

OTHER PUBLICATIONS

Brown, et al., Preprint, A.C.S. Meeting, Minneapolis, Minn., Apr.-1969, pp. B29-B34.

*Primary Examiner*—Joseph Paul Brust

[57] ABSTRACT

A mixture of 3,8- and 4,8-dicyanotricyclo[5.2.1.0]decane is prepared by the hydrocyanation of 8-cyanotricyclo[5.2.1.0]dec-3-ene in the presence of a catalyst system comprising a zero valent nickel complex, free of carbon monoxide, a promoting amount of a metal compound such as zinc chloride and a hydroxy-containing aryl compound such as p-cresol as a solvent.

2 Claims, No Drawings

DICYANOTRICYCLODECANE

1. Field of the Invention

This invention relates to the hydrocyanation of dicyclopentadiene also called tricyclo[5.2.1.0]deca-3,8-diene and to dicyanotricyclodecane.

2. Description of the Prior Art

U.S. Pat. No. 3,778,462 describes the addition of hydrogen cyanide to nonactivated aliphatic double bonds in the presence of a zero valent nickel complex free of carbon monoxide and a promoter such as zinc chloride using a suitable aryl hydroxy-containing solvent such as p-cresol.

SUMMARY OF THE INVENTION

Dicyclopentadiene is readily available as a coproduct from the pyrolysis of liquid hydrocarbons in the manufacture of ethylene. It is also readily available by the dimerization of cyclopentadiene. The structure and numbering for dicyclopentadiene and its derivatives as used herein are

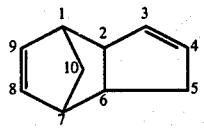

In attempting to hydrocyanate dicyclopentadiene we discovered that monohydrocyanation was much easier to accomplish than dihydrocyanation. Based on this discovery, we developed a two-step procedure for preparing a dicyanotricyclodecane product. A monohydrocyanation reaction is carried out in the first stage of our procedure producing 8-cyanotricyclo[5.2.1.0]dec-3-ene as the exclusive product. No. 3-, 4-, or 9- cyano isomer is produced. In the second stage the dihydrocyanation reaction is completed, producing a mixture of 3,8-dicyanotricyclo[5.2.1.0]decane and 4,8-dicyanotricyclo[5.2.1.0]decane is substantially equal molar amounts.

The hydrocyanation of the dicyclopentadiene to produce the 8-cyanotricyclo[5.2.1.0]dec-3-ene can be a relatively mild hydrocyanation catalyst system such as a zero valent nickel complex having the general formula Ni(A$^1$) (A$^2$) (A$^3$) (A$^4$) where A$^1$, A$^2$, A$^3$, and A$^4$ are neutral ligands which may be the same or different and have the formula P(X) (Y) (Z) wherein X and Y are selected from the class consisting of R and OR, and Z has the formula OR, wherein the three R's may be the same or different, and wherein R is selected from the class consisting of alkyl and aryl groups containing up to 18 carbon atoms with aryl being preferred. An especially preferred class of R's are phenyl and chloro, methyl, and methoxy substituted phenyl.

If desired, any of the R's may be cojoined where possible. Thus the preferred neutral ligands of this group are the aryl phosphites such as triphenyl phosphite, tri(m- and p-tolyl)phosphites, tri(m- and p-chlorophenyl)phosphites, tri(m- and p-methoxyphenyl)phosphites, and tri(m- and p-cresyl)-phosphites and mixtures thereof. Under many of the reaction conditions one or more A$^1$, A$^2$, A$^3$, or A$^4$ may become disassociated from the nickel.

The ligands useful in forming the catalyst here may be defined as any atoms or molecules capable of functioning as a sigma-pi bonded partner in one or more coordinate bonds. A description of such ligands may be found in *Advanced Inorganic Chemistry* by F. Albert Cotton and G. Wilkinson, published by Interscience Publishers, a division of John Wiley & Sons, Library of Congress Catalog Card No. 62-14818; particularly on pages 602-606.

In many instances, it is advantageous to have an excess of certain neutral ligands present with respect to the nickel complex. The preferred excess ligands are the aryl phosphites wherein the aryl groups contain up to 18 carbon atoms. Generally, the excess ligand is present in at least a two molar excess as based on the nickel present. The only limit of excess ligand involves practical considerations for it may even be used as the solvent. However, generally there is little advantage to be obtained in using over 300 mol excess of ligand as based on one mol of nickel. The preferred triaryl phosphites for use as excess ligand are triphenyl phosphite, tri(m- and p-tolyl)phosphites, tri(m- and p-methoxyphenyl)phosphites, and tri(m- and p-cresyl)-phosphites, and mixtures thereof. The primary benefit obtained by the use of the excess ligand is to extend the life of the catalyst. Suitable techniques for preparing these nickel complexes are disclosed in U.S. Pat. No. 3,778,462. In the hydrocyanation reaction the mol ratio of the dicyclopentadiene charge stock to the nickel catalyst is preferably within the range of about 10:1 to about 2,000:1.

A solvent for dicyclopentadiene is used in the hydrocyanation reaction. The solvent can include aryl compounds having from six to 20, preferably from six to ten carbon atoms and at least one hydroxyl group and optionally one or more substituents selected from fluorine, chlorine, bromine, iodine, nitro, cyano and hydrocarbon having from one to six carbon atoms such as phenol, p-cresol, resorcinol, beta-naphthol, p-chlorophenol, p-nitrophenol, p-butylphenol, and the like. Other solvents can be used including aromatic hydrocarbons such as benzene, toluene, xylene, ethylbenzene; nitriles such as acetonitrile and benzonitrile; ethers such as dioxane, o-dimethoxybenzene, tetrahydrofuran and dimethoxyethane; chloroaromatic compounds such as o-dichlorobenzene, and the like. The solvent can be used in an amount to provide a solvent to dicyclopentadiene weight ratio up to about 20:1, preferably up to about 10:1.

The hydrocyanation reaction proceeds under well known hydrocyanation conditions. The temperature is not critical and the particular temperature chosen may depend to some extent on the particular catalyst employed, considering, of course, the desired rate of reaction. Generally, temperatures from −25° C. to 200° C. can satisfactorily be employed, with temperatures from 0° to 150° C. being preferred. Reaction pressure is likewise not critical, and atmospheric pressure is suitable. Lower or higher pressures can also be employed, such as from 0.05 to 100 atmospheres, although these higher pressures serve no particular purpose.

The product of this first stage hydrocyanation reaction is 8-cyanotricyclo[5.2.1.0]dec-3-ene. The addition of the second cyano group by hydrocyanation is much more difficult and requires a more active catalyst system than the first hydrocyanation reaction. This more active catalyst system can be obtained by using a promoter for the nickel complex catalyst described above as well as the hydroxyl aryl solvent described above.

The promoter for the nickel complex catalyst is a compound containing a cation of a metal selected from the class consisting of zinc, cadmium, beryllium, aluminum, gallium, indium, silver, titanium, zironium, hafnium, germanium, tin, vanadium, niobium, scandium, chromium, molybdenum, tungsten, manganese, rhenium, palladium, thorium, erbium, iron and cobalt, or mixtures thereof. Preferably, the compound should be at least partially soluble in the system, and also, preferably, should not have an oxidizing tendency since this generally results in at least partial loss of the nickel catalyst.

The anion portion of the compound is preferably selected from the class consisting of halide, i.e., fluoride, chloride, bromide, and iodide, anions of lower fatty acids of from 2 to 7 carbon atoms, $HPO_3^{-2}$, $H_2PO_2^{-}$, $CF_3COO^{-}$, $OSO_2C_7F_{15}^{-}$ and $SO_4^{-}$, etc. Useful organometallic compounds include $(C_2H_5)_3Al_2Cl_3$ and $C_2H_5AlCl_2$. The promoter acts to improve the number of cycles and in certain cases, the yield and rate. The amount of promoter used generally can be varied from about 1:16 to 50:1 molar ratio of promoter to catalyst. The promoter may be used according to several techniques. Thus, while at least some of the promoter may be added to the reaction mixture at the start of the reaction, additional amounts may be added at any point in time during the reaction.

The product of this second stage hydrocyanation reaction is a substantially equal molar mixture of 3,8-dicyanotricyclo[5.2.1.0]decane and 4,8-dicyanotriclo[5.2.1.0]decane.

This isomer mixture can be readily hydrogenated to a mixture of 3,8-bis(aminomethyl)tricyclodecane and 4,8-bis(aminomethyl)tricyclodecane and this mixed diamine can be reacted with an aromatic or aliphatic diacid, such as adipic acid, to form a polyamide resin. The mixed dicyano product can also be converted to a mixture of 3,8-tricyclodecanedimethanol and 4,8-tricyclodecanedimethanol and this diol mixture can be reacted with a suitable polyacid to form a polyester resin. Or the mixed dicyano product can be converted to a mixture of 3,8-tricyclodecane dicarboxylic acid and 4,8-tricyclodecane dicarboxylic acid and this acid mixture can be reacted with a suitable polyol to form a polyester resin. The mixed dicyano product can additionally be converted to a mixture of 3,8-di(isocyanatomethyl)tricyclodecane and 4,8-di(isocyanatomethyl)tricyclodecane by phosgenation for reaction with a suitable polyhydroxy compound such as a poly(oxypropylene)glycol in the preparation of a urethan polymer.

DESCRIPTION OF PREFERRED EMBODIMENTS

EXAMPLE 1

A 25 cc. charge of dicyclopentadiene and 25 cc. of toluene were placed in a 100 cc. glass reactor with a magnetic stirrer. A catalyst consisting of one mmol of tetrakis(tri-p-tolylphosphite)nickel and 5 mmols of tri-p-tolylphosphite was introduced into the reactor. The contents of the reactor were heated to 60° C. and hydrogen cyanide was bubbled through the reaction liquid at atmospheric pressure at a rate of 28 mmols per hour. After six hours the experiment was terminated. Analysis of the contents of the reactor by gas chromatography disclosed the production of 150 mmols of cyanotricyclodec-3-ene. The rate of product formation was 25 mols/hour/mol catalyst. The cyanotricyclodec-3-ene was separated out by fractional distillation and analyzed by carbon-13 nmr spectroscopy. This analysis disclosed that the cyanotricyclodec-3-ene was a 50:50 mixture of 8-exo- and 8-endo-cyanotricyclo[5.2.1.0]dec-3-ene.

EXAMPLE 2

A 25 cc. charge of dicyclopentadiene and 25 cc. of p-cresol were placed in a 100 cc. glass reactor with a magnetic stirrer. A catalyst consisting of one mmol of tetrakis(tri-p-tolylphosphite)nickel, 5 mmols of tri-p-tolylphosphite, and 2 mmols of anhydrous zinc chloride was introduced into the reactor. The contents of the reactor were heated to 60° C. and hydrogen cyanide was bubbled through the reaction liquid at atmospheric pressure at a rate of 89 mmols per hour. After six hours the experiment was terminated. Analysis of the contents of the reactor by gas chromatography disclosed the production of 534 mmols of cyanotricyclodec-3-ene. The rate of product formation was 89 mols/hour/mol catalyst. Analysis of the cyanodicyclopentene fraction by nmr spectroscopy disclosed that it was a 50:50 mixture of 8-exo- and 8-endo-cyanodicyclopentene-3.

This experiment illustrates that the nickel catalyst with zinc chloride and p-cresol solvent is at least more than three times as active as the same nickel catalyst with toluene solvent. This also illustrates that the active catalyst used in the second stage hydrocyanation can also be used in the first stage hydrocyanation. Excess hydrogen cyanide will deactivate the catalyst, therefore, it is added at the rate at which it is used. For this reason, the rapid monohydrocyanation reaction utilizes essentially all of the hydrogen cyanide resulting in no identifiable dicyano compound in the product by the gas chromatographic analysis. The conversion of dicyclopentadiene was 81 percent.

EXAMPLE 3

A 25 cc. charge of the 8-cyanotricyclodec-3-ene and 25 cc. of p-cresol were placed in a 100 cc. glass reactor with a magnetic stirrer. A catalyst consisting of one mmol of tetrakis(tri-p-tolylphosphite)nickel, 5 mmols of tri-p-tolylphosphite, and 2 mmols of anhydrous zinc chloride were introduced into the reactor. The contents of the reactor were heated to 60° C. and hydrogen cyanide was bubbled through the reaction liquid at one atmosphere pressure at a rate of 13 mmols per hour. After six hours the experiment was terminated. Analysis of the contents of the reactor by gas chromatography disclosed the production of 64 mmols of dicyanotricyclodecane. Analysis of this dicyanotricyclodecane fraction by carbon-13 nmr spectroscopy disclosed that it was approximately a 50:50 molar mixture of 3,8-dicyanotricyclo[5.2.1.0]decane and 4,8-dicyanotriclo[5.2.1.0]decane. The mixture of these two isomers is a clear liquid boiling at about 170° C. at 0.5 mm. The conversion of hydrogen cyanide was 100 percent and the conversion of 8-cyanotricyclodec-3-ene was 17.3 percent.

EXAMPLE 4

A 25 cc. charge of the 8-cyanotricyclodec-3-ene and 25 cc. of p-cresol were placed in a 100 cc. glass reactor with a magnetic stirrer. A catalyst consisting of one mmol of tetrakis(tri-p-tolylphosphite)nickel, five mmols of tri-p-tolylphosphite and two mmols of anhydrous zinc chloride were introduced into the reactor. The contents of the reactor were heated to 60° C. and hydrogen cyanide was bubbled through the reaction liquid at one atmosphere pressure at a rate of 28 mmols per hour. Samples were withdrawn from the reactor every 30 minutes by means of a syringe and immediately analyzed for dicyanotricyclodecane (DCT) by gas chromatography. After six hours the experiment was terminated. The results of the analyses are set forth in the following table:

| Time, hrs. | HCN, mmol | DCT, mmol |
| --- | --- | --- |
| 0.5 | 14 | 4.0 |
| 1.0 | 28 | 11.5 |
| 1.5 | 42 | 21.0 |
| 2.0 | 56 | 20.7 |
| 2.5 | 70 | 23.8 |
| 3.0 | 84 | 23.6 |
| 3.5 | 98 | 23.1 |
| 4.0 | 112 | 23.4 |
| 4.5 | 126 | 23.1 |
| 5.0 | 140 | 23.2 |
| 5.5 | 154 | 23.5 |
| 6.0 | 168 | 23.4 |

It is noted that the hydrocyanation of 8-cyanotricyclodec-3-ene is very slow particularly when compared with the hydrocyanation of dicyclopentadiene as set forth in Example 2. Because of this slow rate of reaction, excess hydrogen cyanide deactivated the catalyst as suggested by the above table. The dicyanodicyclopentane was obtained by fractionation and analyzed by carbon-13 nmr spectroscopy. It was found to be approximately a 50:50 molar mixture of 3,8-dicyanotricyclo[5.2.1.0]decane and 4,8-dicyanotricyclo[5.2.1.0]decane.

EXAMPLE 5

A 25 cc. charge of the 8-cyanotricyclodec-3-ene and 25 cc. of toluene were placed in a 100 cc. glass reactor with a magnetic stirrer. A catalyst consisting of one mmol of tetrakis(tri-p-tolylphosphite)nickel and five mmols of tri-p-tolylphosphite were introduced into the reactor. The contents of the reactor were heated to 60° C. and hydrogen cyanide was bubbled through the reaction liquid at one atmosphere pressure at a rate of 13 mmols per hour. After six hours the experiment was terminated. Analysis of the contents of the reactor by gas chromatography disclosed that no dicyanotricyclodecane was formed. The 8-cyanotricyclodec-3-ene was recovered unchanged.

This experiment illustrates that the nickel catalyst in toluene is not sufficient to add a second mol of hydrogen cyanide to prepare dicyanotricyclodecane.

It is to be understood that the above disclosure is by way of specific example and that numerous modifications and variations are available to those of ordinary skill in the art without departing from the true spirit and scope of the invention.

We claim:

1. A mixture of dicyanotricyclodecane isomers comprising 3,8-dicyanotricyclo[5.2.1.0]decane and 4,8-dicyanotricyclo[5.2.1.0]decane.

2. A mixture of dicyanotricyclodecane isomers in accordance with claim 1 in which the isomers comprise about 50 mol percent 3,8-dicyanotricyclo[5.2.1.0]decane and about 50 mol percent 4,8-dicyanotricyclo[5.2.1.0]decane.

* * * * *